United States Patent [19]

Patel

[11] Patent Number: 4,784,639

[45] Date of Patent: Nov. 15, 1988

[54] CATHETER AND METHOD OF INSERTING CATHETER

[76] Inventor: Piyush V. Patel, 3401 Salisbery, Midland, Tex. 79707

[21] Appl. No.: 70,039

[22] Filed: Jul. 6, 1987

[51] Int. Cl.$^4$ .............................................. A61M 25/00
[52] U.S. Cl. ...................................... 604/53; 604/95; 604/280; 128/658
[58] Field of Search .................. 128/348.1, 656–658; 604/53, 93, 95, 280, 281, 282, 96

[56] References Cited

U.S. PATENT DOCUMENTS

| | | |
|---|---|---|
| 3,399,668 | 9/1968 | Lundgren . |
| 4,020,829 | 5/1977 | Willson et al. .................. 128/657 X |
| 4,033,331 | 7/1977 | Guss et al. ...................... 128/657 X |
| 4,169,464 | 10/1979 | Obrez .................................. 128/657 |
| 4,176,662 | 12/1979 | Frazer ............................. 128/657 X |
| 4,275,724 | 6/1981 | Behrstock . |
| 4,403,985 | 9/1983 | Boretos .................................. 604/53 |
| 4,593,690 | 6/1986 | Sheridan et al. . |
| 4,616,652 | 10/1986 | Simpson .......................... 128/657 X |
| 4,712,551 | 12/1987 | Rayhanabad ...................... 604/96 X |

OTHER PUBLICATIONS

Cordis Ducor ® System, Second Edition, 1973, pp. 4 and 5.

*Primary Examiner*—Dalton L. Truluck
*Attorney, Agent, or Firm*—Herbert J. Hammond

[57] ABSTRACT

A catheter having a tubular portion, a corrugated section, and a tubular tip portion. The tip portion may have side holes. A method of inserting the catheter into a selected artery by first inserting the catheter into an artery, until the tip of the catheter is near the selected artery. Then, the proximate end of the catheter is manipulated to bend a corrugated section of the catheter by forcing the tip of the catheter into the wall of the artery and pushing on the proximate end of the catheter. The proximate end of the catheter is then maneuvered to insert the tip of the catheter into the selected artery.

3 Claims, 2 Drawing Sheets

CATHETER AND METHOD OF INSERTING CATHETER

BACKGROUND OF THE INVENTION

1. Field of the Invention

This invention relates in general to medical procedures and equipment. In particular, the invention relates to an improved catheter and a method of inserting a catheter into a selected artery.

2. Description of the Prior Art

Catheters are used in the performance of medical procedures such as coronary angiography and angioplasty. These procedures involve the introduction of a catheter into the aorta, by way of the femoral artery, under local anesthesia. The distal end of the catheter is then inserted into the opening of a selected coronary artery.

In the prior art, each catheter is designed to be inserted into a particular coronary artery. The catheter must have a particular shape in order to be maneuvered into the proper artery. Therefore, several different catheters are required to perform a full cardiac catheterization.

SUMMARY OF THE INVENTION

The catheter and method of the invention allow full cardiac catheterization using only a single catheter, rather than a multitude of catheters. The catheter of the invention has the usual tubular portion, having a proximate end and a distal end. In addition, the catheter also has a corrugated section, connected to the distal end of the tubular portion of the catheter. There may also be an additional tubular tip portion connected to the distal end of the corrugated section of the catheter. This tubular tip portion may have side holes.

The catheter of the invention is inserted into a selected artery by first inserting the catheter into a major artery, such as the femoral artery, until the distal tip of the catheter is near the selected artery. The proximate end of the catheter is then manipulated to bend the corrugated portion of the catheter. The catheter is manipulated by forcing the tip of the catheter into the wall of the major artery. The proximate end of the catheter is then pushed to cause the corrugated portion of the catheter to bend into a selected shape. The proximate end of the catheter can then be maneuvered to insert the tip of the catheter into the selected artery.

DESCRIPTION OF THE PREFERRED EMBODIMENT

Figure 1:
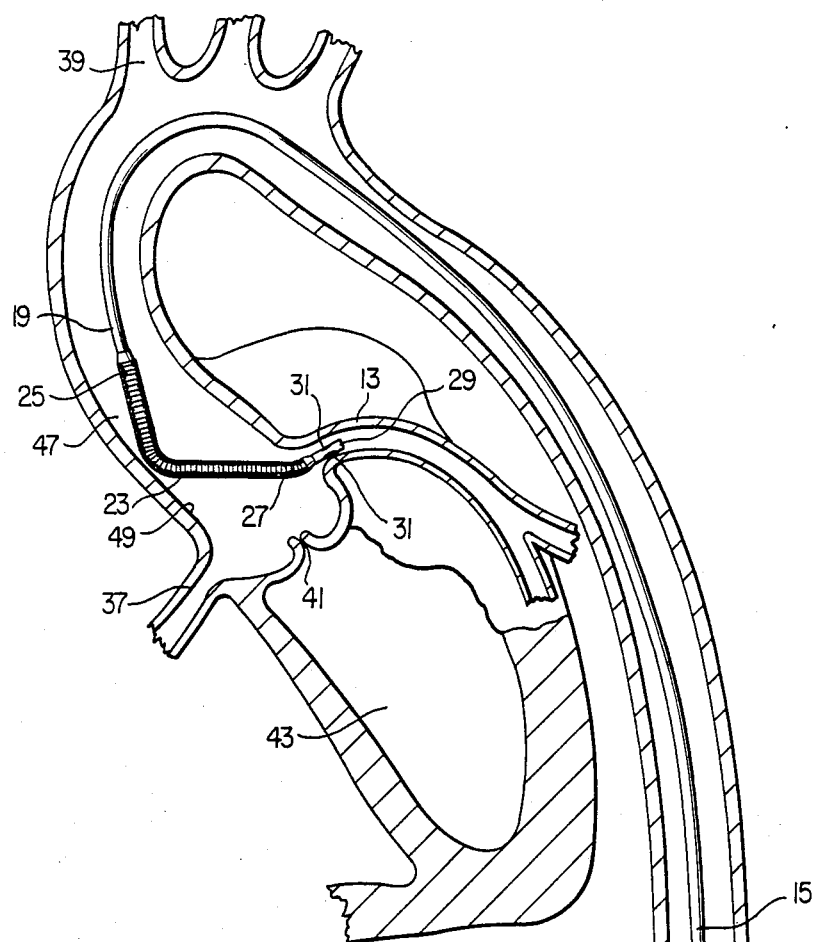
FIG. 1 is a sectional view of the catheter of the invention, inserted into a selected coronary artery.

FIG. 1 shows the catheter 11 of the invention inserted into the left main coronary artery 13. The catheter 11 has a tubular portion 15, having a proximate end 17 and a distal end 19. An attachment 21 is located on the proximate end 17 of the tubular portion 15.

The catheter 11 also has a corrugated section 23, having a proximate end 25 and a distal end 27. The proximate end 25 of the corrugated section 23 is connected to the distal end 19 of the tubular portion 15.

A tubular tip portion 29 is connected to the distal end 27 of the corrugated section 23. The tip portion 29 may have a pair of side holes 31. The side holes 31 pass through the tip portion 29 into the interior 33.

Figure 2:
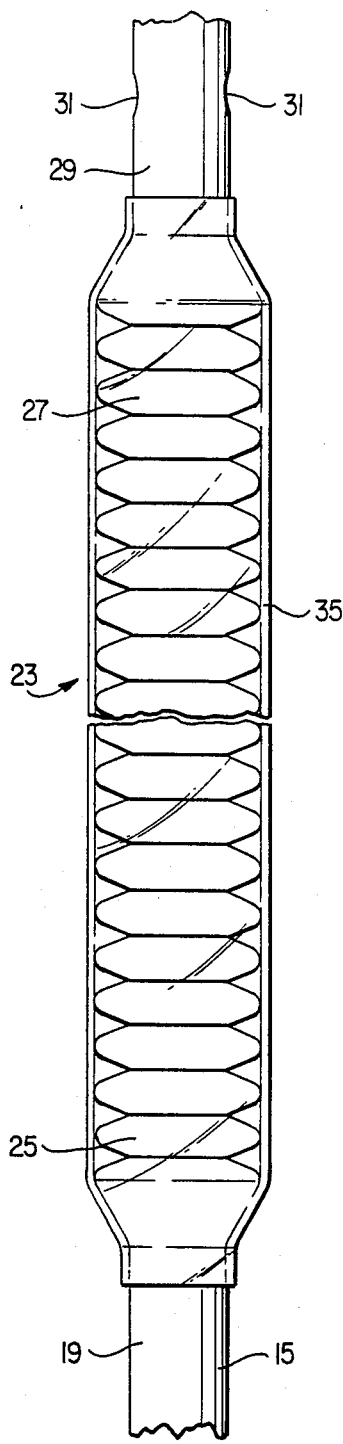
FIG. 2 is a side view of the corrugated portion of the catheter of the invention.
Figure 3:
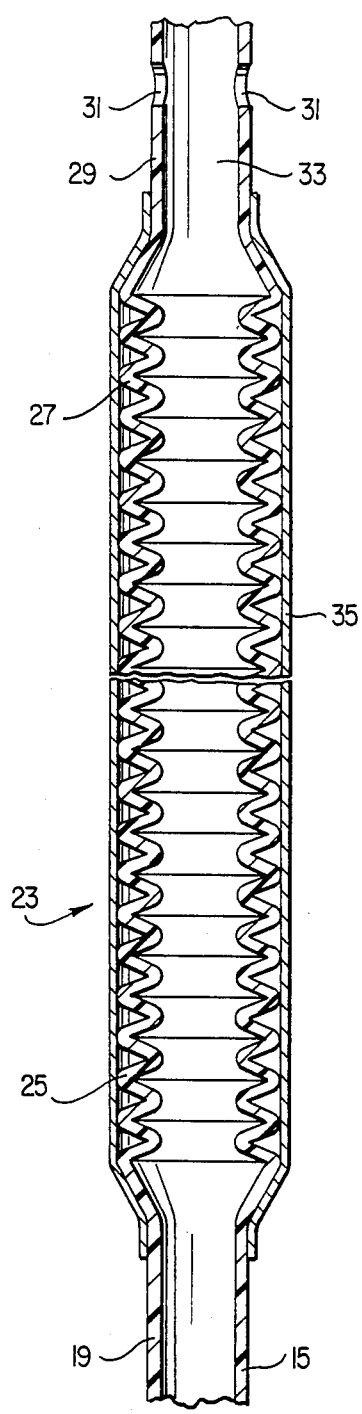
FIG. 3 is a sectional view of the corrugated portion of the catheter of the invention.

FIGS. 2 and 3 show the corrugated section 23 in greater detail. As shown, the corrugated section 23 is covered by a transparent covering 35. This transparent covering 35 facilitates the passing of the corrugated section 23 through the body.

Referring again to FIG. 1, the catheter 11 of the invention may be used to insert the tip portion 29 into any of several locations. One location, as shown, is in the left main coronary artery 13. If desired, the tip portion 29 may also be inserted into the right main coronary artery 37 or the bracheocephalic artery 39. The tip portion 29 may even be inserted through the aortic valve 41 into the left ventrical 43 of the heart.

The method of inserting the catheter 11 into a selected artery involves several steps. First, the catheter 11 is inserted into a patient's femoral artery 45. The catheter 11 is inserted until the tip portion 29 is near the selected artery.

In the case illustrated in FIG. 1, the catheter 11 is inserted until the tip portion 29 is in the aorta 47 near the left main coronary artery 13. The proximate end 17 of the tubular portion 15 is then manipulated to force the tip portion 29 into the wall 49 of the aorta 47 or another artery. The proximate end 17 of the catheter 11 is then pushed to cause the corrugated section 23 to bend to the desired shape. The proximate end 17 of the catheter 11 can then be maneuvered to insert the tip portion 29 of the catheter 11 into the selected artery 13.

The catheter and method of the invention have several advantages over the prior art. The catheter of the invention replaces a plurality of catheters, since a single catheter can be used to insert the tip of the catheter into several different arteries. Therefore, the catheter and method of the invention reduce manufacturing costs and inventories.

Only the preferred embodiment of the invention has been illustrated. It should be understood that the invention is not limited to the embodiment disclosed, but is capable of numerous rearrangements, modifications, and substitutions of parts and elements, without departing from the scope of the invention.

I claim:

1. A method of guiding a coronary angiographic catheter into a selected coronary artery wherein the coronary catheter has a tubular portion with a proximate end and a distal end, a tubular tip, and a flexible corrugated section capable of bending at a predetermined angle having a proximate end connected to the distal end of the tubular portion and a distal end connected to the tubular tip, the method comprising the following steps in order:

inserting the coronary catheter into a femoral artery of a patient;

guiding the coronary catheter through the femoral artery into the coronary artery system of the heart until the tubular tip of the coronary catheter is near the selected coronary artery; and deflecting the tubular tip of the coronary catheter off of an artery wall to bend the flexible corrugated section at an angle sufficient to cause the tubular tip of the coronary catheter to enter the selected coronary artery so that desired angiography and angioplasty can be performed.

2. The method as recited in claim 1, wherein the deflecting step further comprises the steps of:
guiding the tubular tip of the coronary catheter to the artery wall at a predetermined location; and
forcing the tubular tip of the coronary catheter into the artery wall causing the flexible corrugated section to bend at the angle required to cause the tubular tip of the coronary catheter to enter the selected coronary artery.

3. A coronary angiographic catheter comprising:
a tubular portion having a proximate end and a distal end;
a flexible corrugated section having an outer sleeve, a distal end, and a proximate end connected to the distal end of the tubular portion wherein the flexible corrugated section is capable of bending at a predetermined angle for selectively choosing a coronary artery for the coronary catheter to enter; and
a tubular tip portion connected to and projecting from the distal end of the flexible corrugated section and having a side hole whereby the tubular tip portion is deflected off of an artery wall, bending the flexible corrugated section of the coronary catheter at an angle sufficient to cause the tubular tip portion to enter the selected coronary artery for performing angiography and angioplasty.

* * * * *